(12) United States Patent
Cohen et al.

(10) Patent No.: US 12,324,619 B2
(45) Date of Patent: Jun. 10, 2025

(54) AUTOMATIC ANATOMICAL FEATURE IDENTIFICATION AND MAP SEGMENTATION

(71) Applicant: BIOSENSE WEBSTER (ISRAEL) LTD., Yokneam (IL)

(72) Inventors: Assaf Cohen, Kiryat Bialik (IL); Jonathan Yarnitsky, Haifa (IL); Goren Cohn, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 263 days.

(21) Appl. No.: 17/341,267

(22) Filed: Jun. 7, 2021

(65) Prior Publication Data
US 2022/0387099 A1 Dec. 8, 2022

(51) Int. Cl.
*A61B 90/00* (2016.01)
*A61B 18/00* (2006.01)
(Continued)

(52) U.S. Cl.
CPC .......... *A61B 18/1492* (2013.01); *A61B 34/20* (2016.02); *A61B 90/36* (2016.02);
(Continued)

(58) Field of Classification Search
CPC ..... A61B 18/1492; A61B 34/20; A61B 90/36; A61B 2018/00369
See application file for complete search history.

(56) References Cited

U.S. PATENT DOCUMENTS 5,391,199 A 2/1995 Ben-Haim
6,239,724 B1 5/2001 Doron
(Continued)

FOREIGN PATENT DOCUMENTS

EP 2075763 A1 7/2009
EP 1746934 B1 9/2015
(Continued)

OTHER PUBLICATIONS

Paccini, M., Patané, G., & Spagnuolo, M. (2020). Analysis of 3D segmented anatomical districts through grey-levels mapping. Computers & Graphics, 91, 179-188. https://doi.org/10.1016/j.cag.2020.07.015 (Year: 2020).*
(Continued)

*Primary Examiner* — Daniel W Fowler
*Assistant Examiner* — Annie L Shoulders
(74) *Attorney, Agent, or Firm* — Clayton, McKay & Bailey, PC

(57) ABSTRACT

In one embodiment, a medical system includes a catheter configured to be inserted into a heart of a living subject, and including electrodes configured to capture electrical activity of the heart at respective position in the heart, a display, and processing circuitry configured to receive position signals from the catheter, and in response to the position signals compute the respective positions of the electrodes, generate an anatomical map responsively to respective ones of the computed positions, find an anatomical feature of the heart and a position of the anatomical feature responsively to the respective positions of, and electrical activity captured by, respective ones of the electrodes, automatically segment the anatomical map responsively to the found position of the anatomical feature, and render the anatomical map to the display.

15 Claims, 6 Drawing Sheets

(51) Int. Cl.
*A61B 18/14* (2006.01)
*A61B 34/20* (2016.01)

(52) U.S. Cl.
CPC ............ *A61B 2018/00369* (2013.01); *A61B 2034/2059* (2016.02)

(56) References Cited

U.S. PATENT DOCUMENTS

| | | | |
|---|---|---|---|
| 6,332,089 | B1 | 12/2001 | Acker |
| 6,484,118 | B1 | 11/2002 | Govari |
| 6,618,612 | B1 | 9/2003 | Acker |
| 6,690,963 | B2 | 2/2004 | Ben |
| 7,756,576 | B2 | 7/2010 | Levin |
| 7,848,787 | B2 | 12/2010 | Osadchy |
| 7,869,865 | B2 | 1/2011 | Govari et al. |
| 8,320,711 | B2 * | 11/2012 | Altmann ............ A61B 5/061 600/407 |
| 8,494,608 | B2 | 7/2013 | Markowitz |
| 9,259,165 | B2 | 2/2016 | Rubinstein et al. |
| 10,292,588 | B2 | 5/2019 | Ben-Haim |
| 10,918,318 | B2 | 2/2021 | Pryor et al. |
| 2002/0065455 | A1 | 5/2002 | Ben Haim |
| 2003/0120150 | A1 | 6/2003 | Govari |
| 2004/0068178 | A1 | 4/2004 | Govari |
| 2006/0253024 | A1 * | 11/2006 | Altmann ............ G06T 17/00 600/437 |
| 2007/0021679 | A1 | 1/2007 | Narayan |
| 2007/0100332 | A1 | 5/2007 | Paul |
| 2009/0093806 | A1 | 4/2009 | Govari |
| 2009/0138007 | A1 | 5/2009 | Govari |
| 2013/0123652 | A1 | 5/2013 | Rubinstein |
| 2018/0160978 | A1 * | 6/2018 | Cohen ............ A61B 18/1492 |
| 2018/0259608 | A1 | 9/2018 | Golden |
| 2022/0202338 | A1 * | 6/2022 | Zhu ............ A61B 5/35 |

FOREIGN PATENT DOCUMENTS

| | | |
|---|---|---|
| EP | 3741298 A2 | 11/2020 |
| JP | 2012120843 A | 6/2012 |
| WO | WO1996005768 A1 | 2/1996 |
| WO | WO2017192775 A1 | 11/2017 |

OTHER PUBLICATIONS

European Search report for corresponding EPA No. 22177350.0 dated Oct. 21, 2022.

* cited by examiner

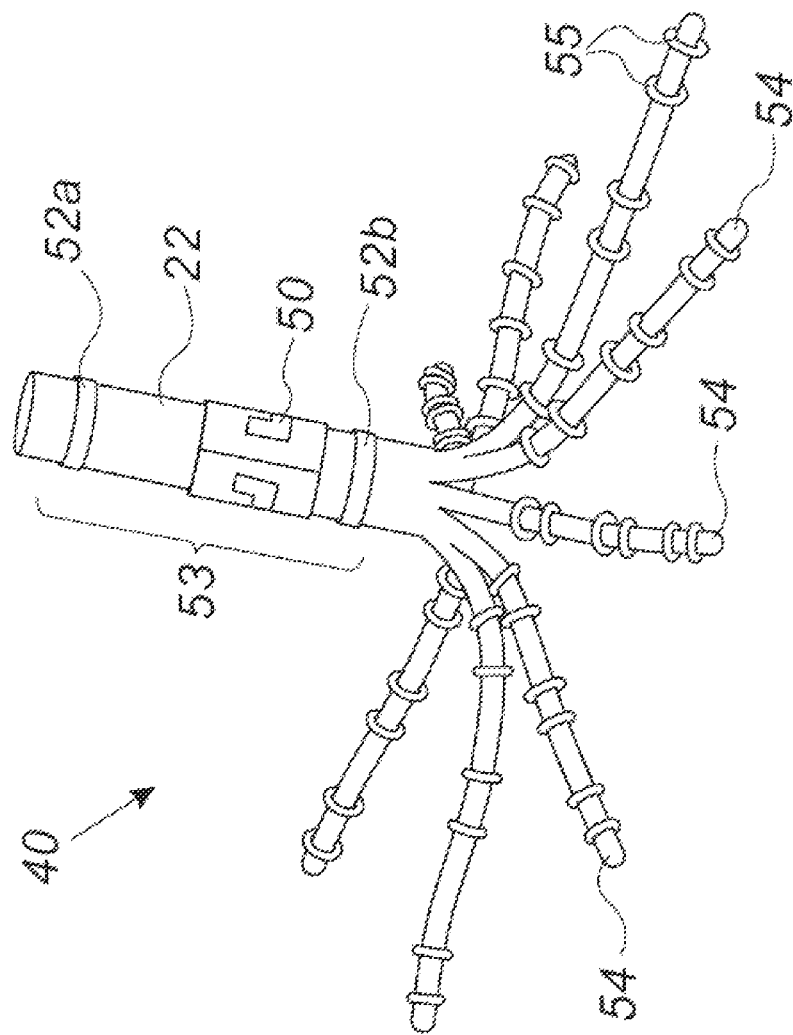

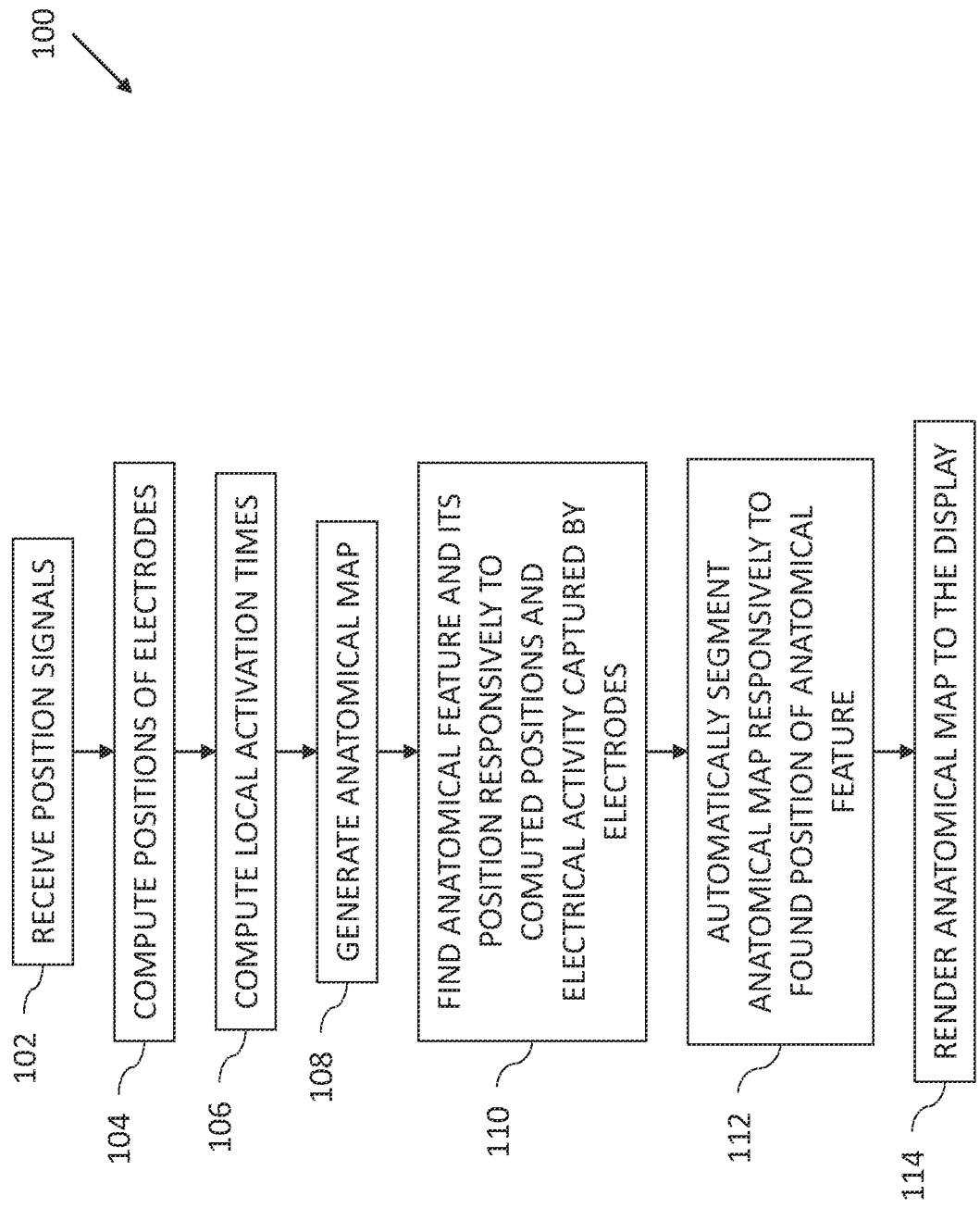

AUTOMATIC ANATOMICAL FEATURE IDENTIFICATION AND MAP SEGMENTATION

FIELD OF THE INVENTION

The present invention relates to medical systems, and in particular, but not exclusively to, catheter-based systems.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178, whose disclosures are all incorporated herein by reference. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied to the tip electrode(s) of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Therefore, when placing an ablation or other catheter within the body, particularly near the endocardial tissue, it is desirable to have the distal tip of the catheter in direct contact with the tissue. The contact can be verified, for example, by measuring the contact between the distal tip and the body tissue. U.S. Patent Application Publication Nos. 2007/0100332, 2009/0093806 and 2009/0138007, describe methods of sensing contact pressure between the distal tip of a catheter and tissue in a body cavity using a force sensor embedded in the catheter.

SUMMARY

There is provided in accordance with an embodiment of the present disclosure, a medical system, including a catheter configured to be inserted into a heart of a living subject, and including electrodes configured to capture electrical activity of the heart at respective positions in the heart, a display, and processing circuitry configured to receive position signals from the catheter, and in response to the position signals compute the respective positions of the electrodes, generate an anatomical map responsively to respective ones of the computed positions, find an anatomical feature of the heart and a position of the anatomical feature responsively to the respective positions of, and the electrical activity captured by, respective ones of the electrodes, automatically segment the anatomical map responsively to the found position of the anatomical feature, and render the anatomical map to the display.

Further in accordance with an embodiment of the present disclosure the processing circuitry is configured to automatically segment the anatomical map leaving a hole in the anatomical map in place of the anatomical feature responsively to the found position of the anatomical feature.

Still further in accordance with an embodiment of the present disclosure the anatomical feature is a heart valve, and the anatomical map includes a map of an atrium, and the processing circuitry is configured to automatically segment the anatomical map leaving a hole in the anatomical map in place of the heart valve.

Additionally, in accordance with an embodiment of the present disclosure the processing circuitry is configured to compute respective local activation times for the electrical activity captured by the electrodes, and find the anatomical feature of the heart and the position of the anatomical feature responsively to the respective positions of, and the computed local activation times of the electrical activity captured by, the respective ones of the electrodes.

Moreover, in accordance with an embodiment of the present disclosure the processing circuitry is configured to automatically segment the anatomical map leaving a hole in the anatomical map in place of the anatomical feature responsively to the found position of the anatomical feature.

Further in accordance with an embodiment of the present disclosure some of the respective local activation times are indicative of atrial electrical activity and some of the respective local activation times are indicative of ventricle electrical activity, and the processing circuitry is configured to find the anatomical feature of the heart responsively to the respective local activation times being indicative of ventricle electrical activity.

Still further in accordance with an embodiment of the present disclosure the anatomical feature is a heart valve, and the anatomical map includes a map of an atrium, and the processing circuitry is configured to automatically segment the anatomical map leaving a hole in the anatomical map in place of the heart valve.

Additionally, in accordance with an embodiment of the present disclosure the catheter includes a shaft and a plurality of flexible arms having respective proximal ends connected to a distal end of the shaft, and the electrodes are disposed at respective locations along each of the flexible arms.

There is also provided in accordance with another embodiment of the present disclosure, a medical method, including receiving position signals from a catheter inserted into a heart of a living subject, the catheter including electrodes to capture electrical activity of the heart at respective positions in the heart, in response to the position signals, computing the respective positions of the electrodes, generating an anatomical map responsively to respective ones of the computed positions, finding an anatomical feature of the heart and a position of the anatomical feature responsively to the respective positions of, and the electrical activity captured by, respective ones of the electrodes, automatically segmenting the anatomical map responsively to the found position of the anatomical feature, and rendering the anatomical map to a display.

Moreover, in accordance with an embodiment of the present disclosure the automatically segmenting includes segmenting the anatomical map leaving a hole in the anatomical map in place of the anatomical feature responsively to the found position of the anatomical feature.

Further in accordance with an embodiment of the present disclosure the anatomical feature is a heart valve, and the anatomical map includes a map of an atrium, and the automatically segmenting includes segmenting the anatomical map leaving a hole in the anatomical map in place of the heart valve.

Still further in accordance with an embodiment of the present disclosure, the method includes computing respective local activation times for the electrical activity captured by the electrodes, wherein the finding includes finding the anatomical feature of the heart and the position of the anatomical feature responsively to the respective positions of, and the computed local activation times of the electrical activity captured by, the respective ones of the electrodes.

Additionally, in accordance with an embodiment of the present disclosure the automatically segmenting includes segmenting the anatomical map leaving a hole in the anatomical map in place of the anatomical feature responsively to the found position of the anatomical feature.

Moreover, in accordance with an embodiment of the present disclosure some of the respective local activation times are indicative of atrial electrical activity and some of the respective local activation times are indicative of ventricle electrical activity, and the finding includes finding the anatomical feature of the heart responsively to the respective local activation times being indicative of ventricle electrical activity.

Further in accordance with an embodiment of the present disclosure the anatomical feature is a heart valve, and the anatomical map includes a map of an atrium, and the automatically segmenting includes segmenting the anatomical map leaving a hole in the anatomical map in place of the heart valve.

Still further in accordance with an embodiment of the present disclosure the catheter includes a shaft and a plurality of flexible arms having respective proximal ends connected to a distal end of the shaft, and the electrodes are disposed at respective locations along each of the flexible arms.

There is also provided in accordance with still another embodiment of the present disclosure, a software product, including a non-transient computer-readable medium in which program instructions are stored, which instructions, when read by a central processing unit (CPU), cause the CPU to receive position signals from a catheter inserted into a heart of a living subject, the catheter including electrodes to capture electrical activity of the heart at respective positions in the heart, in response to the position signals, compute the respective positions of the electrodes, generate an anatomical map responsively to respective ones of the computed positions, find an anatomical feature of the heart and a position of the anatomical feature responsively to the respective positions of, and electrical activity captured by, respective ones of the electrodes, automatically segment the anatomical map responsively to the found position of the anatomical feature, and render the anatomical map to a display.

BRIEF DESCRIPTION OF THE DRAWINGS

The present invention will be understood from the following detailed description, taken in conjunction with the drawings in which:

FIG. 2 is a schematic view of a catheter for use in the system of FIG. 1;

FIG. 9 is a flowchart including steps in a method of operation of the system of FIG. 1.

DESCRIPTION OF EXAMPLE EMBODIMENTS

Overview

Figure 1:
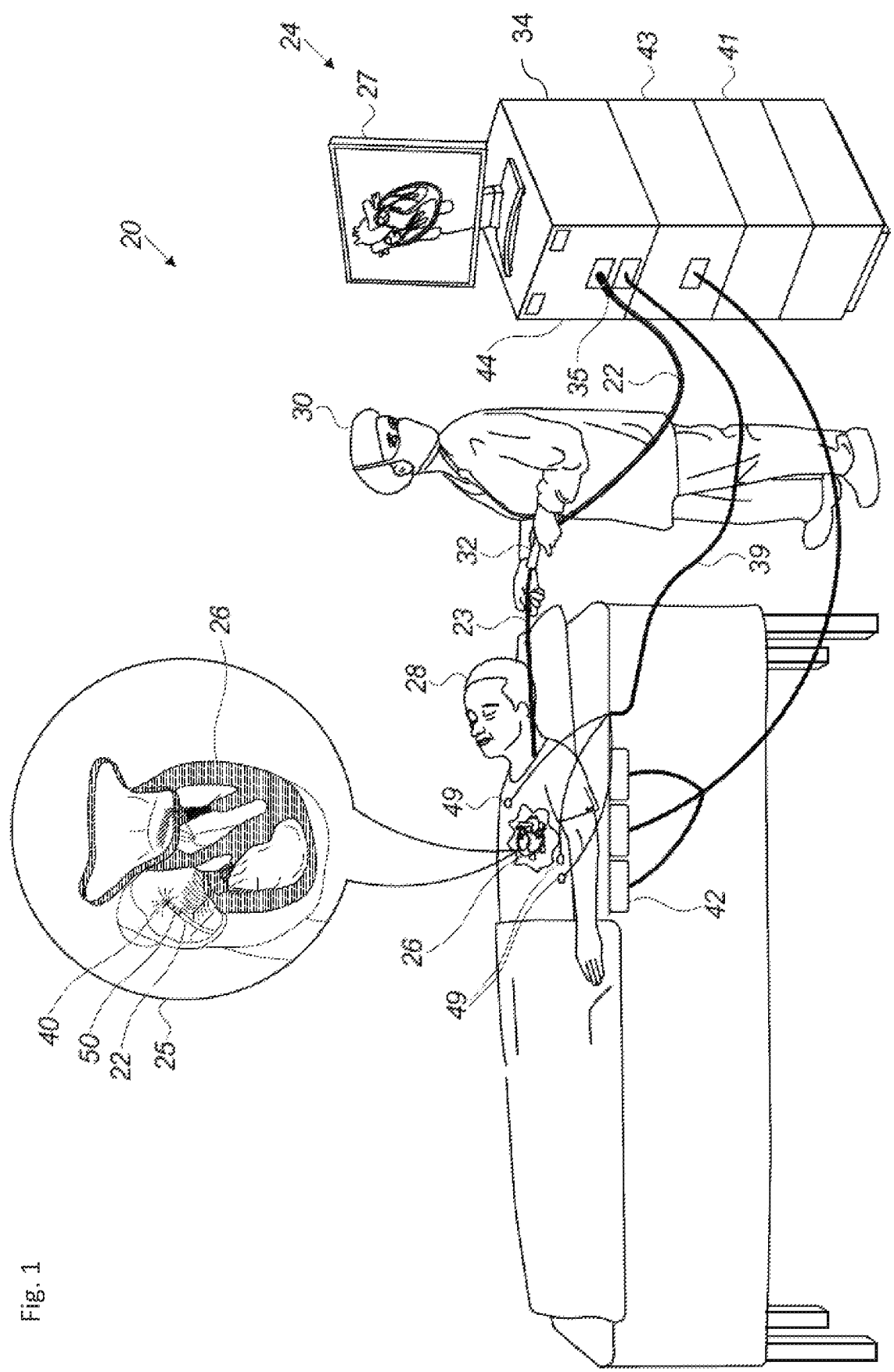
FIG. 1 is a schematic view of a medical procedure system constructed and operative in accordance with an exemplary embodiment of the present invention.

As mentioned previously, in a two-step procedure, mapping followed by ablation, electrical activity at points within the heart is typically sensed and measured by advancing a catheter containing one or more electrodes into the heart, and acquiring data at a multiplicity of points. These data are then utilized to select the target areas at which the ablation is to be performed.

When creating an anatomical structure of either the ventricle or the atrium, the mapping catheter often passes through the valve during mapping, resulting in an unwanted addition to the reconstruction. The physician may manually identify the position of the valve and edit the anatomical structure to remove the valve from the mapped anatomy reconstruction. One solution to enable such a process is for the physician to examine the captured intracardiac signals to determine if the catheter has now entered the valve by seeing if the signals are indicative of being in the ventricle or the atrium. The physician then knows if the catheter is positioned in the valve and the anatomical structure is cropped accordingly. This process is essential for the correctness of the map's LAT coloring or other electro-anatomical mapping process so that the electro-anatomical mapping is across the atrium or ventricle without valves. The manual intervention would be cumbersome for the operator, and may be inaccurate. For example, using a multi-electrode catheter, such as the Pentaray™ (commercially available from Biosense Webster Inc. of Irvine, CA), some of the electrodes of the multi-electrode catheter may be in the valve while others are not, thereby making it difficult for the physician to accurately identify the valve or another anatomical feature.

Embodiments of the present invention solve the above problems by automatically finding an anatomical feature, such as a valve, and automatically segmenting an anatomical map including excluding (or cropping) the anatomical feature from the anatomical map. The segmenting typically includes excluding (or cropping) the anatomical feature from the map while leaving a hole in the map in the place of the anatomical feature instead of assuming that the anatomical feature does not exist at all. For example, a valve is excluded (or cropped) from the map of an atrium leaving a hole in the map of the atrium in the place of the excluded valve.

For example, when mapping with a Pentaray catheter (which includes multiple flexible arms or splines), the catheter is moved around, and at some time during the mapping, some of the arms of the Pentaray may be in the atrium, and some may be in the valve towards the ventricle (or vice-versa). The electrodes of the arms in the atrium capture signals (e.g., intracardiac electrograms (IEGMs)) indicative of atrial activity, and electrodes of the arms in the valve capture signals (e.g., IEGMs) indicative of ventricle activity. The captured signals are analyzed to identify ventricle activity. This may be performed by comparing the timing of the signals (e.g., local activation times of the signals) with the body surface (BS) leads activation timing or any other suitable technique. Additionally, the current location of each catheter electrode may be computed using position tracking techniques. For example, using position tracking based on magnetic tracking, impedance between the catheter electrodes and body surface electrodes, or a combination of magnetic and impedance tracking. Therefore, electrodes exhibiting ventricle activity may be identified as being in the ventricle (e.g., in the valve) and their computed locations (while exhibiting ventricle activity) may be used to automatically, and accurately, segment the map (e.g., crop the valve from the map).

In some embodiments, the electrodes exhibiting ventricle activity provide a cloud of points in 3D space. These locations may then be used to find a bounding structure in 3D which is then segmented, e.g., excluded (or cropped) from the anatomical structure.

The above may be used to find any suitable anatomical feature based on distinguishing electrical activity between different portions of the heart. For example, in some embodiments, the valve may be removed from a map of the ventricle.

Segmenting the anatomical map may include showing the anatomical feature as a separate feature on the anatomical map (e.g., by showing the anatomical feature with a different colored surface and/or with a different level of transparency and/or using dotted lines) or excluding (e.g., cropping) the anatomical feature from the anatomical map.

System Description

Reference is now made to FIG. 1, which is a schematic view of a medical procedure system 20 constructed and operative in accordance with an embodiment of the present invention. Reference is also made to FIG. 2, which is a schematic view of a catheter 40 for use in the system 20 of FIG. 1.

The medical procedure system 20 is used to determine the position of the catheter 40, seen in an inset 25 of FIG. 1 and in more detail in FIG. 2. The catheter 40 includes a shaft 22 and a plurality of flexible arms 54 (only some labeled for the sake of simplicity) having respective proximal ends connected to a distal end of the shaft 22. The catheter 40 is configured to be inserted into a body-part (e.g., a heart 26) of a living subject.

The catheter 40 includes a position sensor 53 disposed on the shaft 22 in a predefined spatial relation to the proximal ends of the flexible arms 54. The position sensor 53 may include a magnetic sensor 50 and/or at least one shaft electrode 52. The magnetic sensor 50 may include at least one coil, for example, but not limited to, a dual-axis or a triple axis coil arrangement to provide position data for location and orientation including roll. The catheter 40 includes multiple electrodes 55 (only some are labeled in FIG. 2 for the sake of simplicity) disposed at respective locations along each of the flexible arms 54 and configured to capture electrical activity of the heart 26 at respective positions in the heart 26. Typically, the catheter 40 may be used for mapping electrical activity in the heart 26 of the living subject using the electrodes 55, or for performing any other suitable function in a body-part of a living subject.

The medical procedure system 20 may determine a position and orientation of the shaft 22 of the catheter 40 based on signals provided by the magnetic sensor 50 and/or the shaft electrodes 52 (proximal-electrode 52a and distal-electrode 52b) fitted on the shaft 22, on either side of the magnetic sensor 50. The proximal-electrode 52a, the distal-electrode 52b, the magnetic sensor 50 and at least some of the electrodes 55 are connected by wires running through the shaft 22 via a catheter connector 35 to various driver circuitries in a console 24. In some embodiments, at least two of the electrodes 55 of each of the flexible arms 54, the shaft electrodes 52, and the magnetic sensor 50 are connected to the driver circuitries in the console 24 via the catheter connector 35. In some embodiments, the distal electrode 52b and/or the proximal electrode 52a may be omitted.

The illustration shown in FIG. 2 is chosen purely for the sake of conceptual clarity. Other configurations of shaft electrodes 52 and electrodes 55 are possible. Additional functionalities may be included in the position sensor 53. Elements which are not relevant to the disclosed embodiments of the invention, such as irrigation ports, are omitted for the sake of clarity.

A physician 30 navigates the catheter 40 to a target location in a body part (e.g., heart 26) of a patient 28 by manipulating the shaft 22 using a manipulator 32 near the proximal end of the catheter 40 and/or deflection from a sheath 23. The catheter 40 is inserted through the sheath 23, with the flexible arms 54 gathered together, and only after the catheter 40 is retracted from the sheath 23, the flexible arms 54 are able to spread and regain their intended functional shape. By containing flexible arms 54 together, the sheath 23 also serves to minimize vascular trauma on its way to the target location.

Console 24 comprises processing circuitry 41, typically a general-purpose computer and a suitable front end and interface circuits 44 for generating signals in, and/or receiving signals from, body surface electrodes 49 which are attached by wires running through a cable 39 to the chest and to the back, or any other suitable skin surface, of the patient 28.

Console 24 further comprises a magnetic-sensing subsystem. The patient 28 is placed in a magnetic field generated by a pad containing at least one magnetic field radiator 42, which is driven by a unit 43 disposed in the console 24. The magnetic field radiator(s) 42 is configured to transmit alternating magnetic fields into a region where the body-part (e.g., the heart 26) is located. The magnetic fields generated by the magnetic field radiator(s) 42 generate direction signals in the magnetic sensor 50. The magnetic sensor 50 is configured to detect at least part of the transmitted alternating magnetic fields and provide the direction signals as corresponding electrical inputs to the processing circuitry 41.

In some embodiments, the processing circuitry 41 uses the position-signals received from the shaft electrodes 52, the magnetic sensor 50 and the electrodes 55 to estimate a position of the catheter 40 inside an organ, such as inside a cardiac chamber. In some embodiments, the processing circuitry 41 correlates the position signals received from the electrodes 52, 55 with previously acquired magnetic location-calibrated position signals, to estimate the position of the catheter 40 inside a cardiac chamber. The position coordinates of the shaft electrodes 52 and the electrodes 55 may be determined by the processing circuitry 41 based on, among other inputs, measured impedances, or on proportions of currents distribution, between the electrodes 52, 55 and the body surface electrodes 49. The console 24 drives a display 27, which shows the distal end of the catheter 40 inside the heart 26.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1.

The Carto®3 system applies an Active Current Location (ACL) impedance-based position-tracking method. In some embodiments, using the ACL method, the processing circuitry 41 is configured to create a mapping (e.g., current-position matrix (CPM)) between indications of electrical impedance and positions in a magnetic coordinate frame of the magnetic field radiator(s) 42. The processing circuitry 41 estimates the positions of the shaft electrodes 52 and the electrodes 55 by performing a lookup in the CPM.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description.

The catheter 40 described above includes eight flexible arms 54 with six electrodes 55 per arm 54. Any suitable catheter may be used instead of the catheter 40, for example, a catheter with a different number of flexible arms and/or electrodes per arm, or a different probe shape such as a balloon catheter or a lasso catheter, by way of example only.

The medical procedure system 20 may also perform ablation of heart tissue using any suitable catheter, for example using the catheter 40 or a different catheter and any suitable ablation method. The console 24 may include an RF signal generator 34 configured to generate RF power to be applied by an electrode or electrodes of a catheter connected to the console 24, and one or more of the body surface electrodes 49, to ablate a myocardium of the heart 26. The console 24 may include a pump (not shown), which pumps irrigation fluid into an irrigation channel to a distal end of a catheter performing ablation. The catheter performing the ablation may also include temperature sensors (not shown) which are used to measure a temperature of the myocardium during ablation and regulate an ablation power and/or an irrigation rate of the pumping of the irrigation fluid according to the measured temperature.

Figure 3:
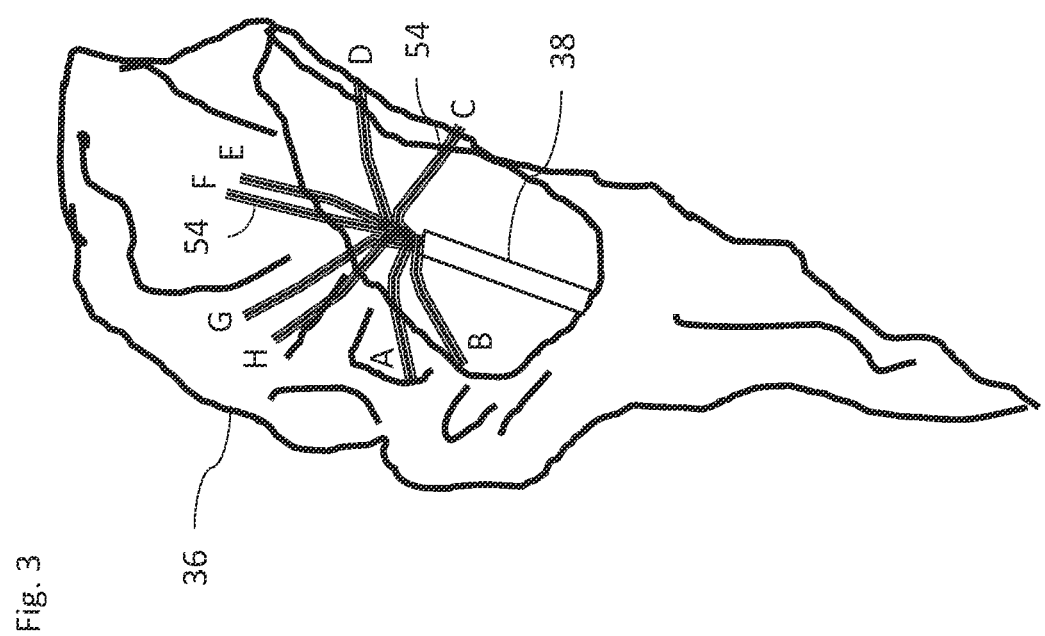
FIG. 3 is a schematic view of an anatomical map and the catheter of FIG. 2.

Reference is now made to FIG. 3, which is a schematic view of an anatomical map 36 and a representation 38 of the catheter 40 of FIG. 2. FIG. 3 shows that most of the flexible arms 54 (labeled A, B, D-H) of the catheter 40 are in the atrium of the heart 26 while one of the flexible arms 54 (labeled arm C) is in the valve towards the ventricle. For the sake of simplicity, the example of FIG. 3 shows that only one of the flexible arms 54, arm C, is in the valve and that all (the electrodes) of arm C is in the valve. In other scenarios, part of one of the flexible arms 54, or more than one of the flexible arms 54 (or part thereof) may be in the valve or other anatomical feature which is selected for exclusion from the anatomical map 36. The anatomical map 36 shown in FIG. 3 is of one of the atria. In some embodiments, the anatomical map 36 may be of one of the ventricles or any other suitable body part.

Figure 4:
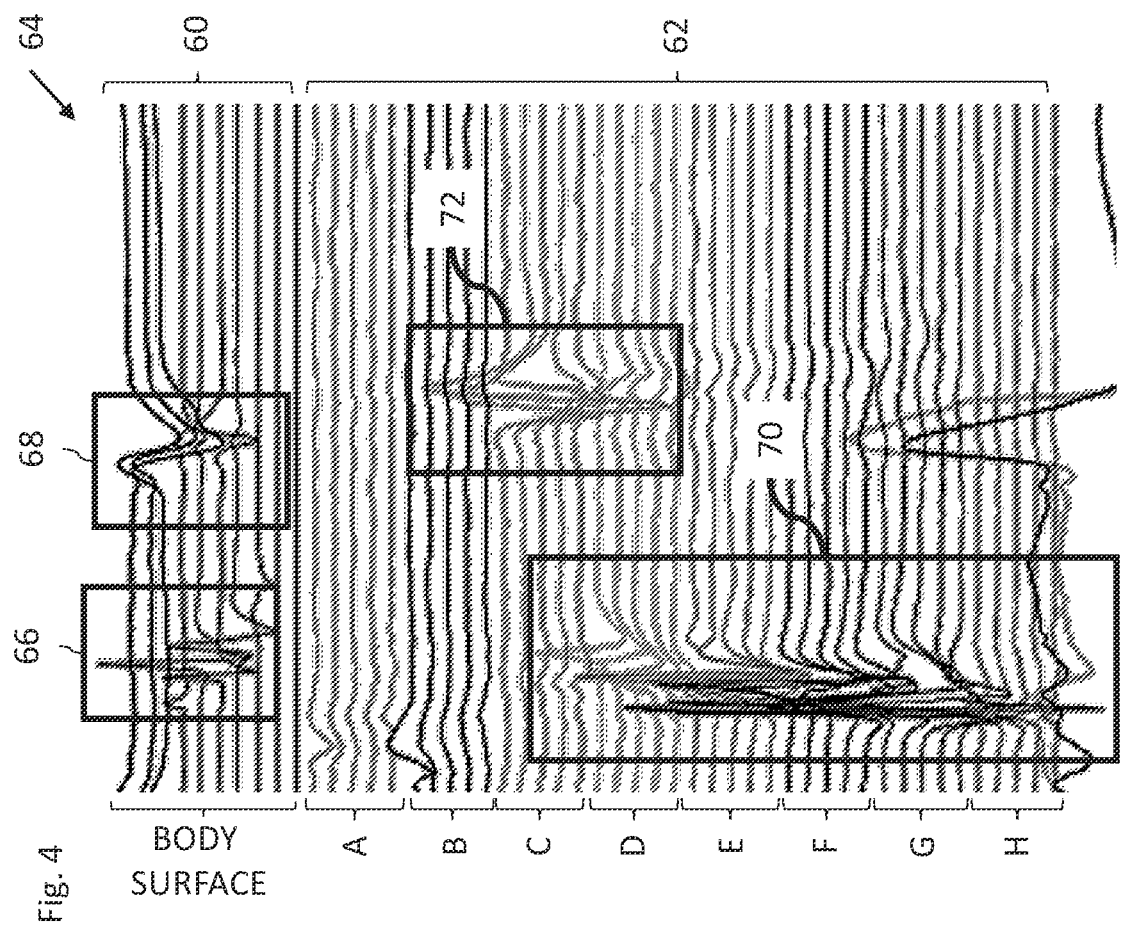
FIG. 4 is a schematic view of electrical activation signals captured via electrodes of the catheter of FIG. 2 in the position shown in FIG. 3 and body surface electrodes.

Reference is now made to FIG. 4, which is a schematic view of a window of interest 64 (e.g., one heartbeat cycle) of electrical activation signals 60, 62 captured via electrodes 55 of the catheter 40 of FIG. 2 in the position shown in FIG. 3 and body surface electrodes 49 (FIG. 1). FIG. 4 shows electrocardiograms (ECGs) 60 captured by the body surface electrodes 49 and intracardiac electrograms (IEGMs) 62 captured by the electrodes 55 of the catheter 40. The IEGM 62 are ordered in FIG. 4 according to the flexible arms 54 of the catheter 40 (i.e., arms A-H) and according to the order of the electrodes 55 on each of the flexible arms 54. Groups of the IEGM 62 are labeled with A-H according to the corresponding labels of the flexible arms 54 as shown in FIG. 3.

FIG. 3 shows that the electrocardiograms 60 captured by the body surface electrodes 49 are exhibiting both atrial activity (block 66) and ventricle activity (block 68). The electrodes 55 of arms A and B are showing very little electrical activity which may be indicative of the electrodes 55 of arms A and B not being in contact with tissue of the heart 26, or in insufficient contact with the tissue. The electrodes 55 of arms D-H are exhibiting atrial activity (block 70) while the electrodes 55 of arms C are exhibiting ventricle activity (block 72).

The difference between atrial activity and ventricle activity seen in the IEGMs 62 may be indicated by the respective time values of the respective local activation times of the respective IEGMs 62 in the window of interest 64. Generally, ventricle activity is later in the window of interest 64 than the atrial activity.

Figure 5:
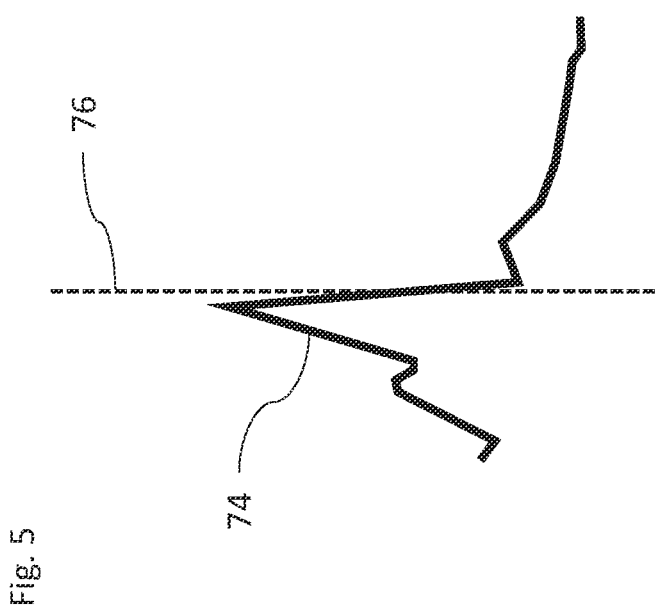
FIG. 5 is a schematic view of an electrical activation signal and its associated local activation time.

Reference is now made to FIG. 5, which is a schematic view of an electrical activation signal 74 and its associated local activation time 76. The electrical activation signal 74 is an example of one of the IEGMs 62 of FIG. 4. The local activation time 76 of the electrical activation signal 74 may be computed using any suitable method for example by computing the maximum negative slope of the electrical activation signal 74 (for example based on differentiating the signal) and setting the local activation time 76 to be equal to the time of the computed maximum negative slope. A method for determination of reference annotation time from multi-channel electrocardiogram (ECG) signals is described in U.S. Pat. No. 9,259,165 to Rubinstein, et al. Accurate time annotation of intracardiac ECG signals is described in US Patent Publication 2013/0123652 of Rubinstein.

Figure 6:
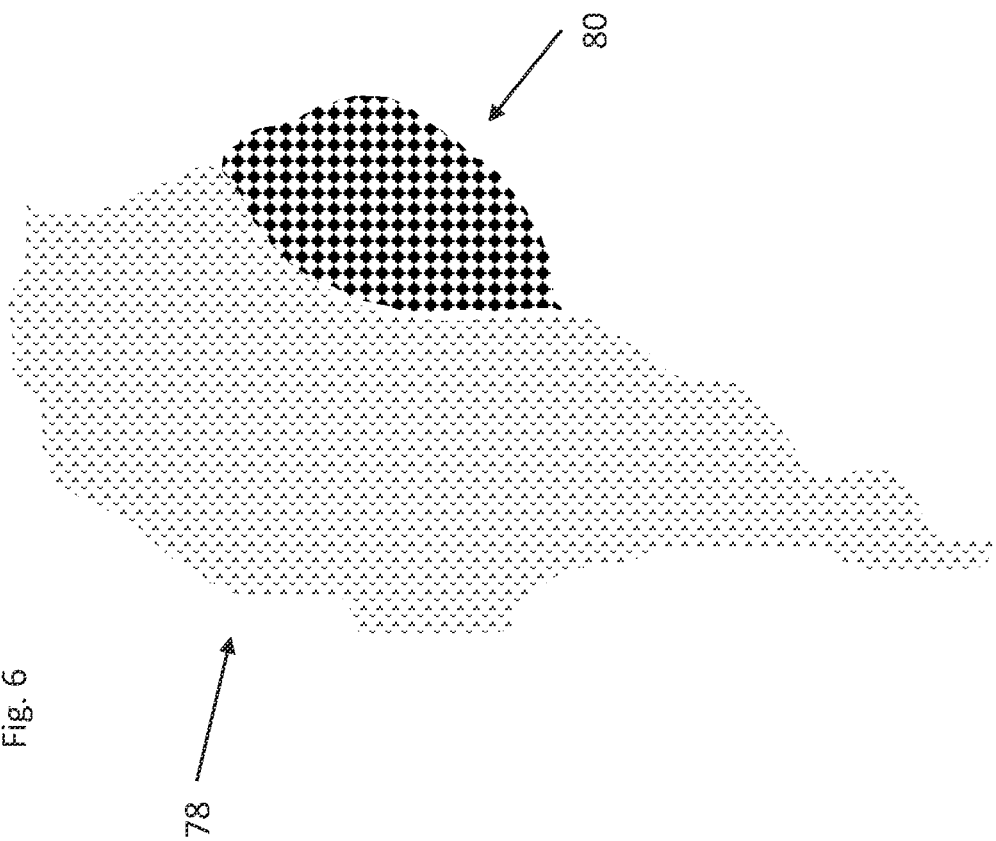
FIG. 6 is a schematic view of computed electrode positions for use in the system of FIG. 1.

Reference is now made to FIG. 6, which is a schematic view of computed electrode positions for use in the system 20 of FIG. 1. FIG. 6 shows electrode positions 78 in one of the atria of the heart 26 and electrode positions 80 in a valve of the heart 26 computed for the electrodes 55 of the catheter 40 over time. The positions 78, 80 may be computed using any suitable position tracking method, for example, using magnetic-based tracking, a distribution of current or impedance measurements, or any suitable combination thereof. Therefore, moving the catheter 40 around the heart 26 or in a chamber of the heart 26, generates a 3D cloud of computed positions 78, 80 over time, which may then be used to generate an anatomical map of the heart 26 as described in more detail below.

Figure 7:
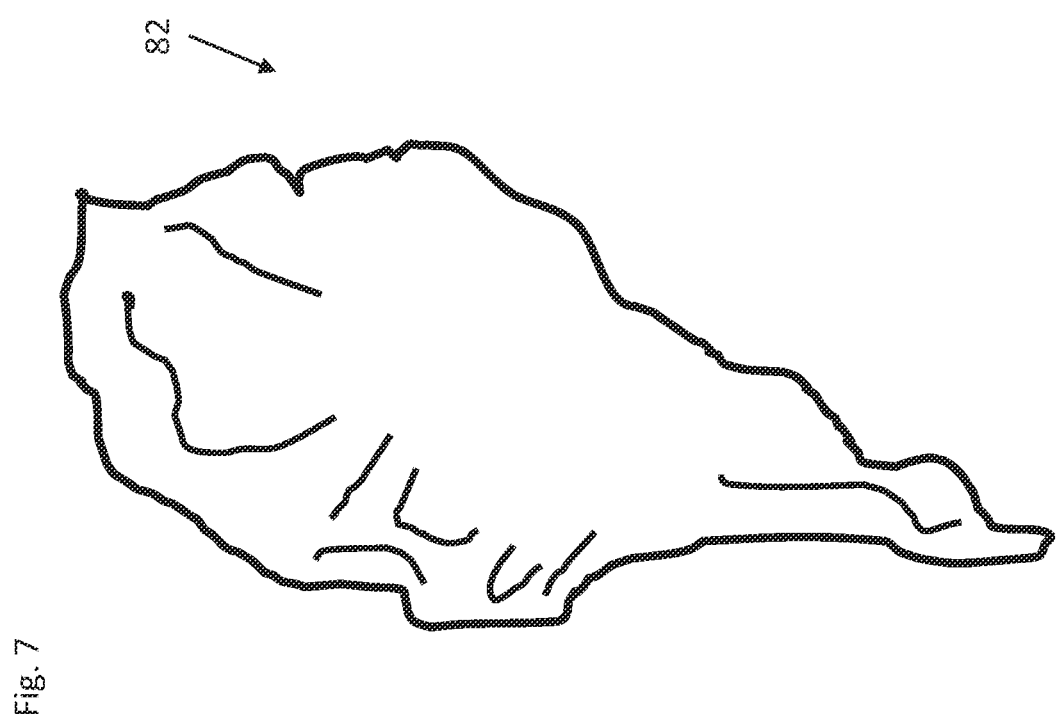
FIG. 7 is a schematic view of a first anatomical map based on some of the electrode positions of FIG. 6.

Reference is now made to FIG. 7, which is a schematic view of a first anatomical map 82 based on some of the electrode positions of FIG. 6. The anatomical map 82 may be generated using any suitable anatomical map generation method, for example, but not limited to, Fast Anatomical Mapping (FAM). FAM is described in U.S. Pat. No. 10,918,310 to Cohen, et al. In FAM, a smooth shell is generated around a three-dimensional (3D) cloud of data points. The anatomical map 82 may be generated by generating a smooth shell around the computed electrode positions 78 (FIG. 6) of the atrium, while ignoring the electrode positions 80 of the valve. In such a manner, the anatomical map 82 provides a closed shell describing the atrium and ignores the valve and places a shell surface where the entrance to the valve would be in the atrium. Although the anatomical map 82 may be useful in many scenarios, ignoring the opening of the valve is incorrect in other scenarios, for example, where an electro-anatomical map, such as a LAT map, is generated based on the shell surface of the anatomical map 82. In such a case, the LAT map would show propagation of the electrical activation wave across the opening of the atrium into the valve and that is incorrect.

Figure 8:
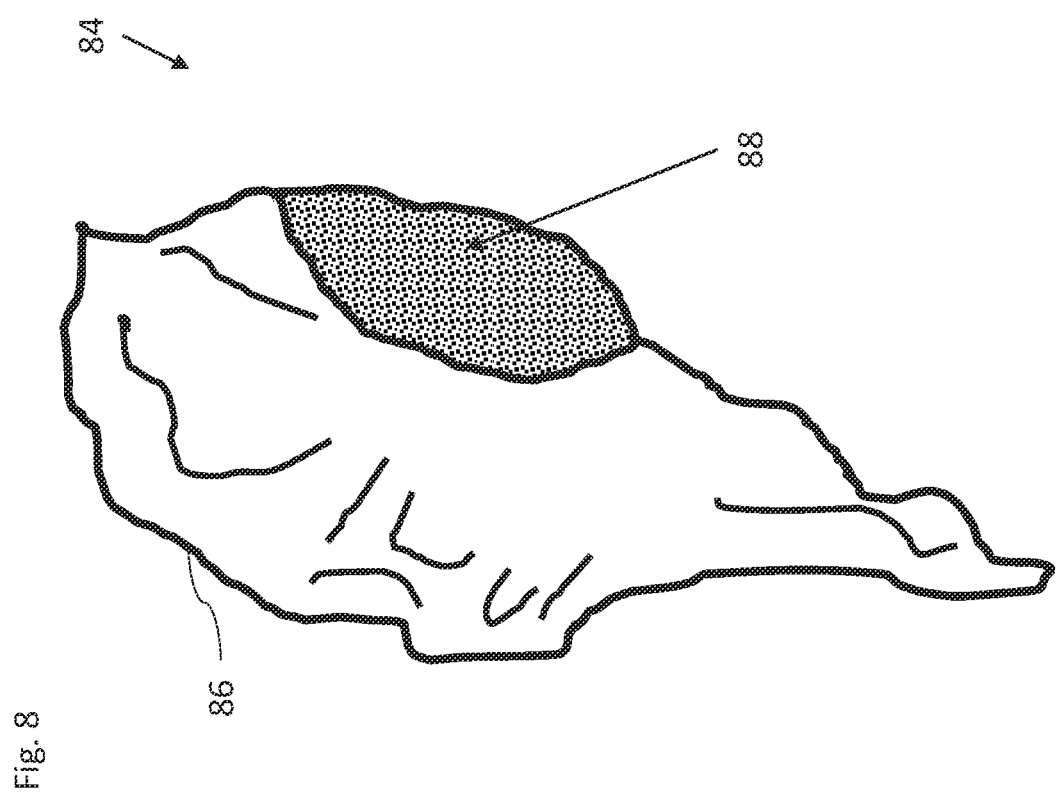
FIG. 8 is a schematic view of a second anatomical map based on some of the electrode positions of FIG. 6.

Reference is now made to FIG. 8, which is a schematic view of a second anatomical map 84 based on some of the electrode positions 78, 80 of FIG. 6. The anatomical map 84 is generated based on generating a smooth shell 86 around the electrode positions 78 of the atrium while taking into account the electrode positions 80 of the valve so that an opening 88 is left in the smooth shell 86 corresponding to the opening of the valve from the atrium. In such a case, a LAT map would correctly show propagation of the electrical activation wave across the surface of the atrium, but not across the opening into the valve.

Reference is now made to FIG. 9, which is a flowchart 100 including steps in a method of operation of the system 20 of FIG. 1. Reference is also made to FIGS. 1 and 2.

The catheter 40 is moved around the heart 26 or a chamber thereof, and the processing circuitry 41 is configured to receive (block 102) position signals from the catheter 40 as the catheter 40 is moved around the heart 26 or a chamber thereof. The position signals may be received by the processing circuitry 41 directly from the electrodes 55 and/or from the magnetic sensor 50 and/or from the electrode(s) 52 via the shaft 22. Additionally, or alternatively, the position signals may be received by the processing circuitry 41 from the body surface electrodes 49 which receives signals from the electrodes 52, 55. In response to receiving the position signals, the processing circuitry 41 is configured to compute (block 104) the respective positions 78, 80 (FIG. 6) of the electrodes 55 (as the catheter 40 is moved around the heart 26 over time) using any suitable position tracking method.

The processing circuitry 41 is configured to compute (block 106) respective local activation times (LATs) for the electrical activity captured by the electrodes 55 at the various positions of the catheter 40 over time. The LATs may be computed using any suitable method, for example, by computing the respective maximum negative slopes of the IEGMs 62 (FIG. 4). In some cases, for example, the illustration provided in FIG. 4, some of the respective local activation times are indicative of atrial electrical activity and some of the respective local activation times are indicative of ventricle electrical activity.

The processing circuitry 41 is configured to generate (block 108) the anatomical map 36 (FIG. 3) responsively to respective ones of the computed positions 78, 80. For example, Fast Anatomical Mapping (FAM) may be used to generate the anatomical map. FAM is described in U.S. Pat. No. 10,918,310 to Cohen, et al. Any suitable anatomic map generation method may be used.

The processing circuitry 41 is configured to find (block 110) an anatomical feature of the heart 26 (e.g., a part of the heart such as a heart valve) and a position of the found anatomical feature responsively to the respective positions 80 of, and the electrical activity captured by, respective ones of the electrodes 50 at the various positions of the catheter 40 over time. For example, the electrical activity captured by at least some of the electrodes 55 (at various times) may be indicative of electrical activity of an anatomical feature, e.g., ventricle activity, and the respective electrode positions associated with this electrical activity (e.g., ventricle electrical activity) indicate the position of the found anatomical feature (e.g., a valve) In some embodiments, the processing circuitry 41 is configured to find the anatomical feature of the heart (e.g., a part of the heart such as a heart valve) and the position of the anatomical feature responsively to the respective positions of, and the computed local activation times (e.g., indicating atrial versus ventricle electrical activity) of the electrical activity captured by, respective ones of the electrodes 55 at the various positions of the catheter 40 over time. In some embodiments, the processing circuitry 41 is configured to find the anatomical feature of the heart (e.g., a heart valve) responsively to the respective local activation times being indicative of ventricle electrical activity.

The processing circuitry 41 is configured to automatically segment (block 112) the anatomical map 36 responsively to the found position of the anatomical feature. The processing circuitry 41 is configured to automatically segment the anatomical map 36 by showing the anatomical feature as a separate feature on the anatomical map 36 (e.g., by showing the anatomical feature with a different colored surface and/or with a different level of transparency and/or using dotted lines) or excluding (e.g., cropping) the anatomical feature from the anatomical map 36.

In some embodiments, the processing circuitry 41 is configured to automatically segment the anatomical map 36 leaving a hole (e.g., opening 88 of FIG. 8) in the anatomical map 36 in place of the anatomical feature responsively to the found position of the anatomical feature. In some embodiments, when the found anatomical feature is a heart valve and the anatomical map 36 includes a map of an atrium, the processing circuitry 41 is configured to automatically segment the anatomical map 36 leaving a hole in the anatomical map of the atrium in place of the heart valve. The processing circuitry 41 is configured to render (block 114) the anatomical map to the display 27.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical system for automatic anatomical feature identification and map segmentation, the system comprising:
   a catheter configured to be inserted into a heart of a living subject, and including electrodes configured to capture electrical activity of the heart at respective positions in the heart;
   a display; and
   processing circuitry configured to:
      receive position signals from the catheter, and in response to the position signals compute the respective positions of the electrodes;
      generate an anatomical map responsively to respective ones of the computed positions;
      find an anatomical feature of the heart and a position of the anatomical feature responsively to the respective positions of, and the electrical activity captured by, respective ones of the electrodes;
      automatically segment the anatomical map responsively to the found position of the anatomical feature, where automatically segmenting the anatomical map comprises:
         i) computing respective local activation times for the electrical activity captured by the electrodes; and
         ii) identifying in the local activation times activity associated with the anatomical feature; and
      render the anatomical map, as segmented to distinguish the anatomical feature, to the display.

2. The system according to claim 1, wherein the processing circuitry is configured to automatically segment the anatomical map leaving a hole in the anatomical map in place of the anatomical feature responsively to the found position of the anatomical feature.

3. The system according to claim 2, wherein: the anatomical feature is a heart valve, and the anatomical map includes a map of an atrium; and the processing circuitry is configured to automatically segment the anatomical map leaving a hole in the anatomical map in place of the heart valve.

4. The system according to claim 1, wherein the processing circuitry is configured to automatically segment the anatomical map leaving a hole in the anatomical map in place of the anatomical feature responsively to the found position of the anatomical feature.

5. The system according to claim 1, wherein:
   some of the respective local activation times are indicative of atrial electrical activity and some of the respective local activation times are indicative of ventricle electrical activity; and
   the processing circuitry is configured to find the anatomical feature of the heart responsively to the respective local activation times being indicative of ventricle electrical activity.

6. The system according to claim 5 wherein the anatomical feature is a heart valve, and the anatomical map includes a map of an atrium; and the processing circuitry is configured to automatically segment the anatomical map leaving a hole in the anatomical map in place of the heart valve.

7. The system according to claim 1, wherein:
   the catheter includes a shaft and a plurality of flexible arms having respective proximal ends connected to a distal end of the shaft; and
   the electrodes are disposed at respective locations along each of the flexible arms.

8. A medical method for automatic anatomical feature identification and map segmentation, the method comprising:
   receiving position signals from a catheter inserted into a heart of a living subject, the catheter including electrodes to capture electrical activity of the heart at respective positions in the heart;
   in response to the position signals, computing the respective positions of the electrodes;
   generating an anatomical map responsively to respective ones of the computed positions;
   finding an anatomical feature of the heart and a position of the anatomical feature responsively to the respective positions of, and the electrical activity captured by, respective ones of the electrodes;
   automatically segmenting the anatomical map responsively to the found position of the anatomical feature, where automatically segmenting the anatomical map comprises:
      i) computing respective local activation times for the electrical activity captured by the electrodes; and
      ii) identifying in the local activation times activity associated with the anatomical feature; and
   render the anatomical map, as segmented to distinguish the anatomical feature, to the display.

9. The method according to claim 8, wherein the automatically segmenting includes segmenting the anatomical map leaving a hole in the anatomical map in place of the anatomical feature responsively to the found position of the anatomical feature.

10. The method according to claim 9, wherein:

the anatomical feature is a heart valve, and the anatomical map includes a map of an atrium; and the automatically segmenting includes segmenting the anatomical map leaving a hole in the anatomical map in place of the heart valve.

11. The method according to claim 8, wherein the automatically segmenting includes segmenting the anatomical map leaving a hole in the anatomical map in place of the anatomical feature responsively to the found position of the anatomical feature.

12. The method according to claim 8, wherein:

some of the respective local activation times are indicative of atrial electrical activity and some of the respective local activation times are indicative of ventricle electrical activity; and the finding includes finding the anatomical feature of the heart responsively to the respective local activation times being indicative of ventricle electrical activity.

13. The method according to claim 12, wherein:

the anatomical feature is a heart valve, and the anatomical map includes a map of an atrium; and the automatically segmenting includes segmenting the anatomical map leaving a hole in the anatomical map in place of the heart valve.

14. The method according to claim 8, wherein:

the catheter includes a shaft and a plurality of flexible arms having respective proximal ends connected to a distal end of the shaft; and the electrodes are disposed at respective locations along each of the flexible arms.

15. A software product, comprising a non-transient computer-readable medium in which program instructions are stored, which instructions, when read by a central processing unit (CPU), cause the CPU to:

receive position signals from a catheter inserted into a heart of a living subject, the catheter including electrodes to capture electrical activity of the heart at respective positions in the heart;

in response to the position signals, compute the respective positions of the electrodes;

generate an anatomical map responsively to respective ones of the computed positions;

find an anatomical feature of the heart and a position of the anatomical feature responsively to the respective positions of, and electrical activity captured by, respective ones of the electrodes;

automatically segment the anatomical map responsively to the found position of the anatomical feature, where automatically segmenting the anatomical map comprises:

i) computing respective local activation times for the electrical activity captured by the electrodes; and ii) identifying in the local activation times activity associated with the anatomical feature; and render the anatomical map to a display.

* * * * *